US012653530B2

(12) United States Patent
   Kucklick

(10) Patent No.: US 12,653,530 B2
(45) Date of Patent: Jun. 16, 2026

(54) STAPLE AND DRIVER FOR TENDON STAPLING APPARATUS

(71) Applicant: KiriGenX, Inc., Phoenix, AZ (US)

(72) Inventor: Theodore R. Kucklick, Scotts Valley, CA (US)

(73) Assignee: KiriGenX, Inc., Phoenix, AZ (US)

( * ) Notice: Subject to any disclaimer, the term of this patent is extended or adjusted under 35 U.S.C. 154(b) by 0 days.

(21) Appl. No.: 18/733,425

(22) Filed: Jun. 4, 2024

(65) Prior Publication Data

US 2024/0398408 A1     Dec. 5, 2024

Related U.S. Application Data

(60) Provisional application No. 63/506,178, filed on Jun. 5, 2023.

(51) Int. Cl.
   *A61B 17/064*     (2006.01)
   *A61B 17/068*     (2006.01)
   *A61B 17/00*      (2006.01)

(52) U.S. Cl.
   CPC ...... *A61B 17/0684* (2013.01); *A61B 17/0642* (2013.01); *A61B 17/0644* (2013.01); *A61B 2017/00836* (2013.01); *A61B 2017/0084* (2013.01); *A61B 2017/00862* (2013.01); *A61B 2017/00867* (2013.01); *A61B 2017/0645* (2013.01)

(58) Field of Classification Search
   CPC ........... A61B 17/0684; A61B 17/0642; A61B 17/0644; A61B 2017/00836; A61B 2017/0084; A61B 2017/00862; A61B 2017/00867; A61B 2017/0645; A61B 17/068; A61B 17/10; A61B 17/105; A61B 2017/00004; A61B 2017/00336; A61B 2017/0647; A61B 2090/08021
   USPC ......... 227/175.1–182.1, 8, 19; 606/139, 142, 606/143, 205–208
   See application file for complete search history.

(56) References Cited

U.S. PATENT DOCUMENTS 5,013,316 A * 5/1991 Goble ................... A61F 2/0811
                                                     606/916
5,156,609 A * 10/1992 Nakao ................... A61B 17/10
                                                     606/205

(Continued)

FOREIGN PATENT DOCUMENTS

CA         2208360 A1 * 6/1996 ......... A61B 17/0643
WO     WO-2004000105 A2 * 12/2003 ........... A61B 17/064

(Continued)

OTHER PUBLICATIONS

International Search Report and Written Opinion dated Sep. 26, 2024 from IA No. PCT/US2024/032442.

*Primary Examiner* — Robert F Long
(74) *Attorney, Agent, or Firm* — Crockett & Crockett, PC; K. David Crockett, Esq.; Niky Economy Syrengelas, Esq.

(57)          ABSTRACT

An improved surgical stapling apparatus for inserting a staple into a shoulder tendon or bone to treat a shoulder tendon tear. The surgical stapling apparatus also includes a surgical stapling assembly having a pointed driver having a housing and having a proximal and a distal end and at least one staple having a proximal end and a distal end that is loaded within the driver. The driver drives a staple through an augmentation patch into tendon or bone.

4 Claims, 8 Drawing Sheets

(56)                References Cited

U.S. PATENT DOCUMENTS

| | | | | | |
|---|---|---|---|---|---|
| 5,352,229 | A | * | 10/1994 | Goble | A61B 17/0642 606/220 |
| 5,354,292 | A | * | 10/1994 | Braeuer | A61F 2/0063 606/1 |
| 5,425,490 | A | * | 6/1995 | Goble | A61B 17/0642 606/86 R |
| 5,439,479 | A | * | 8/1995 | Shichman | A61B 17/0643 606/220 |
| 5,573,543 | A | * | 11/1996 | Akopov | A61B 17/04 227/176.1 |
| 5,584,859 | A | * | 12/1996 | Brotz | A61B 17/08 606/228 |
| 5,797,714 | A | * | 8/1998 | Oddenino | F16B 21/08 411/509 |
| 5,931,855 | A | * | 8/1999 | Buncke | B26D 3/08 606/228 |
| 6,099,537 | A | * | 8/2000 | Sugai | A61B 17/1285 606/205 |
| 6,149,660 | A | * | 11/2000 | Laufer | A61B 17/0684 606/139 |
| 6,193,733 | B1 | * | 2/2001 | Adams | A61B 17/1285 606/151 |
| 6,554,852 | B1 | * | 4/2003 | Oberlander | A61B 17/0401 606/232 |
| 6,835,206 | B2 | * | 12/2004 | Jackson | A61F 2/4611 623/908 |
| 6,989,016 | B2 | * | 1/2006 | Tallarida | A61B 17/3439 227/175.1 |
| 7,481,832 | B1 | * | 1/2009 | Meridew | A61B 17/0401 606/232 |
| 7,670,362 | B2 | * | 3/2010 | Zergiebel | B25B 23/101 606/311 |
| 7,749,250 | B2 | * | 7/2010 | Stone | A61B 17/0482 606/232 |
| 7,828,820 | B2 | * | 11/2010 | Stone | A61B 17/0401 606/232 |
| 7,862,573 | B2 | * | 1/2011 | Darois | B25B 23/065 606/139 |
| 7,896,907 | B2 | * | 3/2011 | McDevitt | A61F 2/0811 606/68 |
| 7,918,879 | B2 | * | 4/2011 | Yeung | A61B 17/0642 606/139 |
| 8,235,995 | B2 | * | 8/2012 | Focht | A61B 17/068 606/75 |
| 9,033,201 | B2 | * | 5/2015 | Euteneuer | A61B 17/0642 606/139 |
| 9,107,661 | B2 | * | 8/2015 | Euteneuer | A61B 17/56 |
| 9,271,726 | B2 | * | 3/2016 | Euteneuer | A61B 17/17 |
| 9,370,356 | B2 | * | 6/2016 | Euteneuer | A61F 2/0811 |
| 9,585,656 | B2 | * | 3/2017 | Taber | A61B 17/0682 |
| 10,123,796 | B2 | * | 11/2018 | Westling | A61B 17/0642 |
| 11,045,190 | B1 | * | 6/2021 | Anakwenze | A61B 17/0401 |
| 11,304,704 | B2 | * | 4/2022 | Thomas | A61B 17/2909 |
| 11,357,497 | B1 | * | 6/2022 | Anakwenze | A61B 17/0642 |
| 12,011,154 | B1 | * | 6/2024 | Anakwenze | A61B 17/068 |
| 2002/0049456 | A1 | * | 4/2002 | Coleman | A61B 17/0644 606/139 |
| 2002/0138146 | A1 | * | 9/2002 | Jackson | A61F 2/4455 623/17.11 |
| 2005/0055027 | A1 | * | 3/2005 | Yeung | A61B 17/0644 606/75 |
| 2005/0085857 | A1 | * | 4/2005 | Peterson | A61B 17/0644 606/213 |
| 2005/0165421 | A1 | * | 7/2005 | Wilson | A61B 17/1222 606/151 |
| 2005/0240222 | A1 | * | 10/2005 | Shipp | A61B 17/068 606/219 |
| 2006/0129154 | A1 | * | 6/2006 | Shipp | A61B 17/0644 606/301 |
| 2006/0241622 | A1 | * | 10/2006 | Zergiebel | C08L 67/04 606/908 |
| 2008/0167667 | A1 | * | 7/2008 | Criscuolo | A61B 17/122 606/151 |
| 2008/0173691 | A1 | * | 7/2008 | Mas | A61B 17/0057 227/175.1 |
| 2008/0177300 | A1 | * | 7/2008 | Mas | A61B 17/0057 606/151 |
| 2009/0001121 | A1 | * | 1/2009 | Hess | F02D 41/3094 227/175.1 |
| 2009/0030434 | A1 | * | 1/2009 | Paz | A61B 17/064 606/1 |
| 2009/0134198 | A1 | * | 5/2009 | Knodel | A61B 17/0684 227/176.1 |
| 2010/0187283 | A1 | * | 7/2010 | Crainich | A61B 17/0682 227/175.1 |
| 2010/0191258 | A1 | * | 7/2010 | Harris | A61B 17/0684 227/175.1 |
| 2010/0292715 | A1 | * | 11/2010 | Nering | A61B 17/0682 606/151 |
| 2010/0312250 | A1 | * | 12/2010 | Euteneuer | A61B 17/0642 606/99 |
| 2011/0034953 | A1 | * | 2/2011 | Milo | A61F 2/2445 606/213 |
| 2011/0257635 | A1 | * | 10/2011 | Whitman | A61B 17/00 606/1 |
| 2012/0211543 | A1 | * | 8/2012 | Euteneuer | A61B 17/07207 227/175.1 |
| 2012/0241490 | A1 | * | 9/2012 | Busch | A01K 11/002 227/76 |
| 2012/0248171 | A1 | * | 10/2012 | Bailly | A61B 17/068 227/176.1 |
| 2013/0109910 | A1 | * | 5/2013 | Alexander | A61B 17/42 600/204 |
| 2013/0153627 | A1 | * | 6/2013 | Euteneuer | A61F 2/0811 227/175.1 |
| 2014/0364908 | A1 | * | 12/2014 | Mayer | A61B 17/0401 606/232 |
| 2016/0051252 | A1 | * | 2/2016 | Smith | A61B 17/0466 606/232 |
| 2016/0120542 | A1 | * | 5/2016 | Westling | A61B 17/0642 227/175.1 |
| 2019/0154070 | A1 | * | 5/2019 | Kargenian | B25C 5/15 |
| 2021/0275290 | A1 | * | 9/2021 | Domecus | A61F 2/0811 |
| 2021/0338235 | A1 | | 11/2021 | Euteneuer et al. | |
| 2023/0139487 | A1 | | 5/2023 | Gustafson et al. | |
| 2025/0114201 | A1 | * | 4/2025 | Brauon | A61F 2/2466 |

FOREIGN PATENT DOCUMENTS

| | | | | |
|---|---|---|---|---|
| WO | WO2021084407 | | 5/2021 | |
| WO | WO-2021084407 | A1 * | 5/2021 | A61B 17/0401 |

* cited by examiner

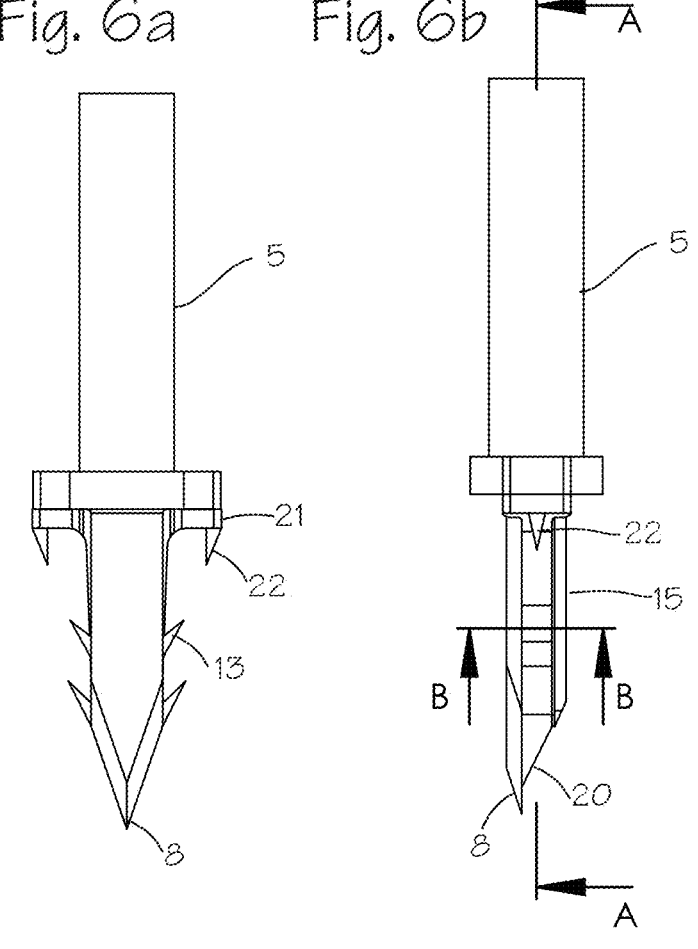
Fig. 6a
Fig. 6b
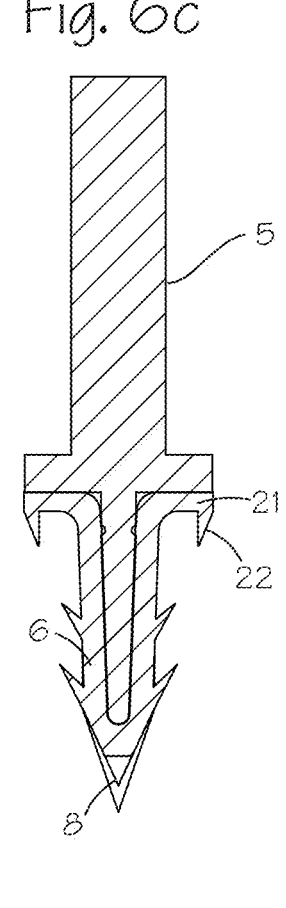
Fig. 6c
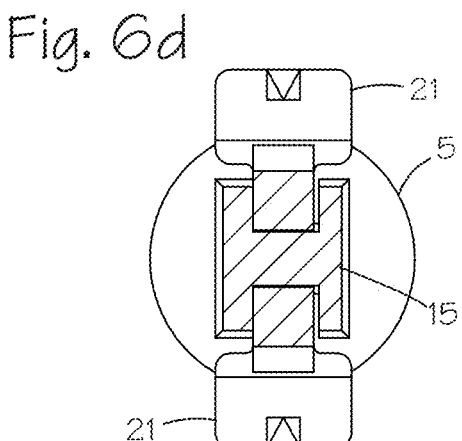
Fig. 6d

STAPLE AND DRIVER FOR TENDON STAPLING APPARATUS

This application claims priority to U.S. Provisional Application 63/506,178 filed Jun. 5, 2023.

FIELD OF THE INVENTIONS

The inventions described below relate to the field of a surgical stapling apparatus including a surgical assembly and driver for driving a staple through an augmentation patch into tendon or bone.

BACKGROUND OF THE INVENTIONS

Tendon repair procedures are common and require the use of a staple or other securing device to attached the tenson back to the bone or tissue for repair. Currently tendon repair with biologic sheet augmentation includes two-prong staples for securing augmentation patches to reattach torn or damaged tendon to bone or other soft tissue. Staples typically have 2 prongs that penetrate the tendon and anchor it securely to the bone or tissue. A strap connects the two prongs to help maintain their position and provide support to the repair site. The two prong staples have disadvantage in cases where tendon and bone have irregular anatomy, it is challenge to achieve proper placement and fixation with two-prong staple. In cases where the tendon is small, the two-prong staple can cause excessive damage or fail to adequately fix to the bone or tissue, or can back out and require surgical retrieval.

SUMMARY

The devices and methods described below provide for an improved stapler with driver used with a surgical stapling apparatus for stronger and more secure placement of the staple to torn tissue or bone for securing and placing of a staple through an augmentation patch into torn bone or tendon. Surgical staples are frequently used to close incisions when cutting through tissue and bone inside the body. Conventional staple systems use U-shaped staples that are pushed through the body along prongs into body tissue along guides. These guides are prone to bending when pushed through the body.

The devices and methods described below provide for an improved staple and driver for driving the staple through an augmentation patch into tendon or bone. The driver has a trocar point for piercing the augmentation patch so that it does not bunch or wad up when driving in a staple.

The staples are loaded onto the driver in an inverted "U" shape where the "U" part is positioned on the distal end of the driver for insertion onto the patient. The staples are pushed in along the "U"-shaped proximal end and the distal end is two legs that include compression flanges. The inverted U-shaped staple is driven through an augmentation patch via the driver and then placed over into torn tendon tissue to provide additional support to the staple when driven through the body to prevent deformation or bending of the staple.

When the staple is loaded onto the driver, the assembly acts like a bone anchor for insertion into tendon or bone. The anchor system includes a monorail I beam driver. The monorail I beam driver is less sensitive to insertion angle and bending than two prong strap staple inserters.

The staple can include a central channel or eyelet through which a suture or anchor is passed or over molded. The "U"

shaped staple includes a center notch that allows for tissue ingrowth to prevent backout of the staple.

BRIEF DESCRIPTION OF THE DRAWINGS

FIG. 6a illustrates the staple when positioned onto the distal end of driver.

FIG. 6b is a side view of FIG. 6a.

FIG. 6c is a cross sectional view along line A-A of FIG. 6b.

FIG. 6d is a cross sectional view along line B-B of FIG. 6b.

DETAILED DESCRIPTION OF THE INVENTIONS

Figure 1:
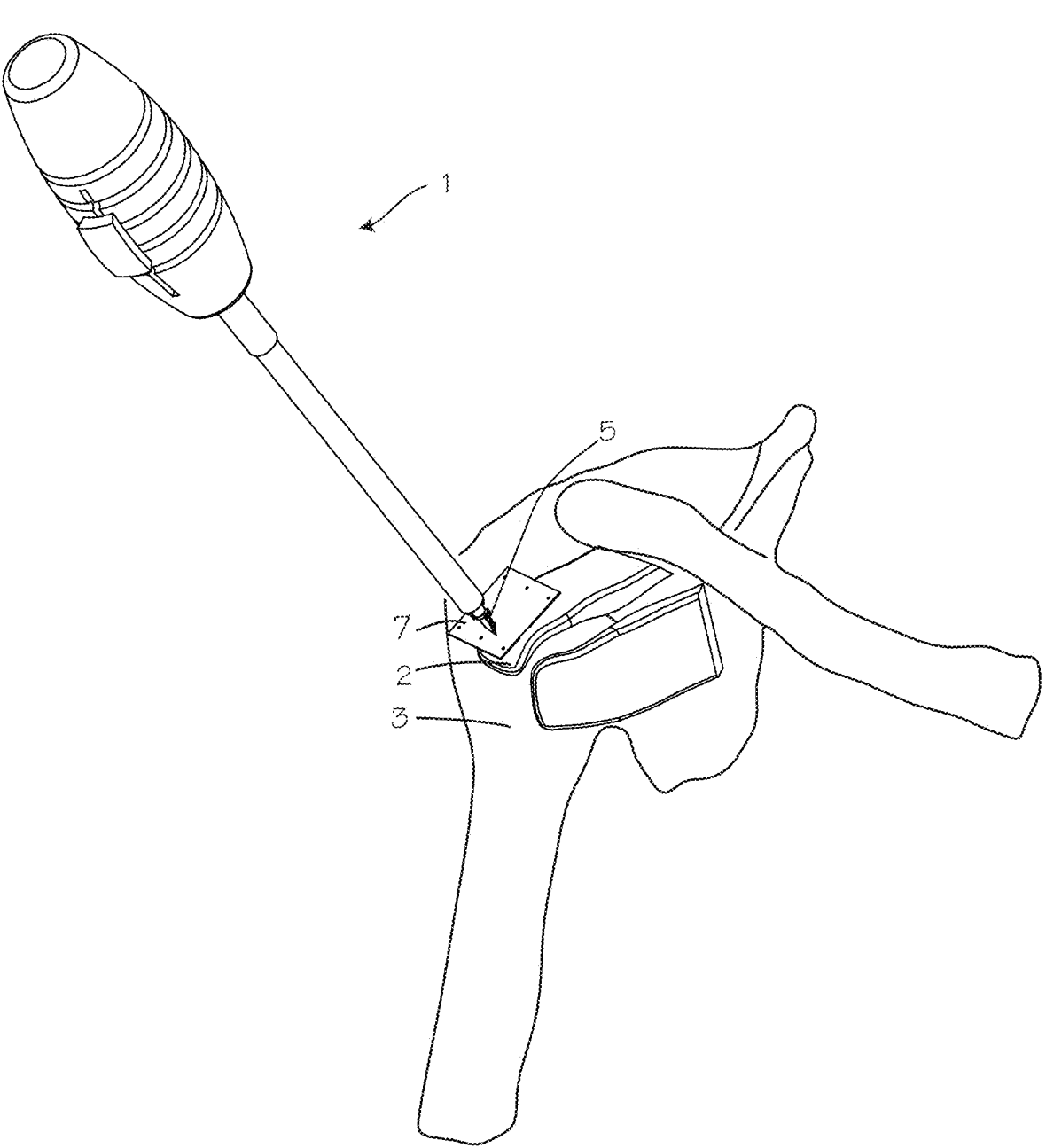
FIG. 1 illustrates a surgical stapling apparatus for inserting a staple into a shoulder tendon or bone to treat a shoulder tendon tear.

FIG. 1 illustrates a surgical stapling apparatus 1 for inserting a staple into a shoulder tendon 2 or bone 3 to treat a shoulder tendon tear. The surgical stapling apparatus includes a surgical stapling assembly 4 (shown in FIG. 2) including a driver 5 and a staple 6 within the driver at the distal end of the surgical stapling assembly. Surgery to repair tendons is performed arthroscopically. An augmentation patch 7 or sheet made of synthetic materials or biological tissues is placed over torn tendon and driven, via a staple, into bone or tendon by having the driver pierce the augmentation patch via trocar piercing point 8 at end of driver. The staple is driven through the augmentation patch into the tendon or bone to secure the augmentation patch to the torn tissue. The augmentation patch supports the torn tendon to advanced healing.

Figure 2:
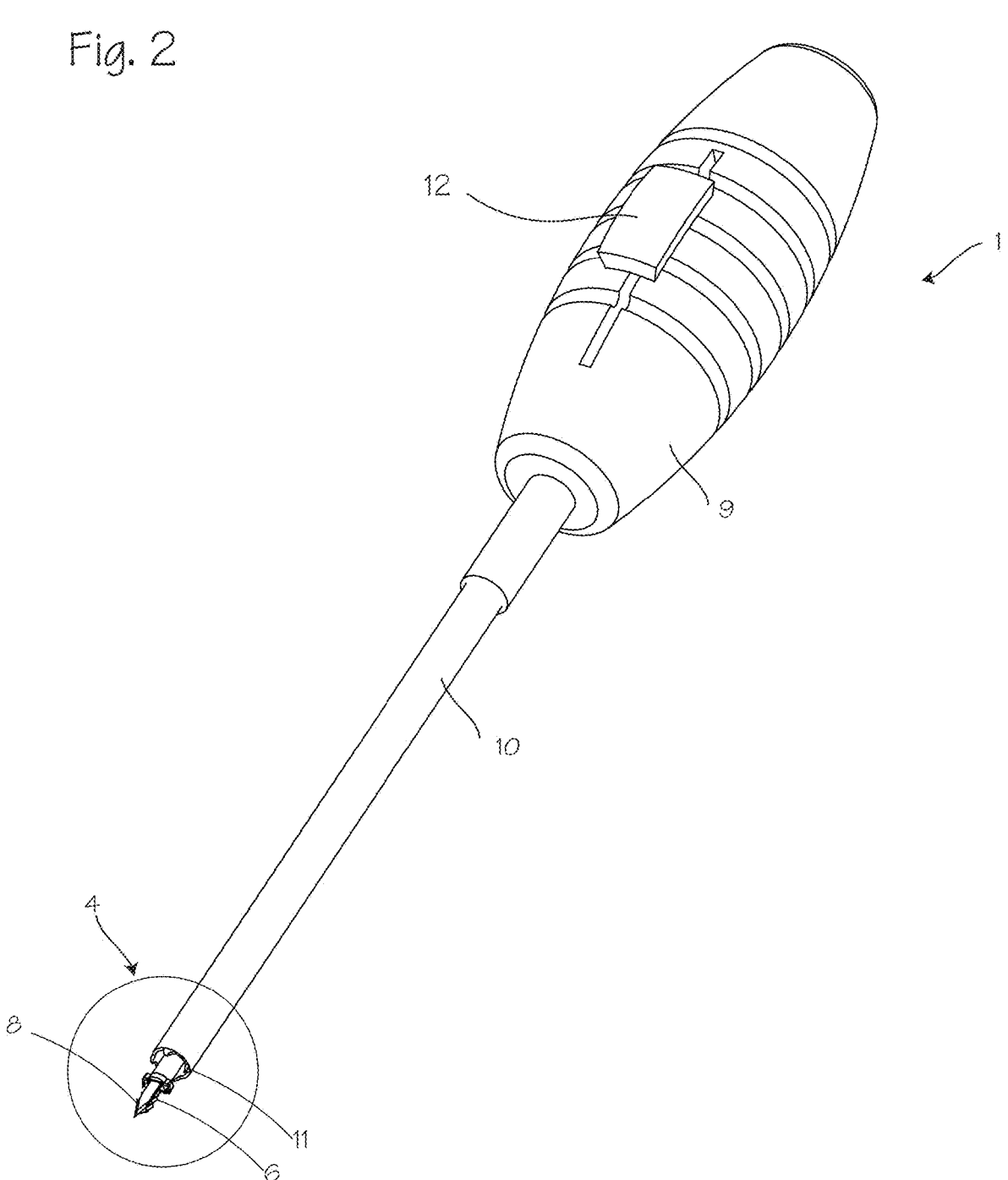
FIG. 2 illustrates a surgical stapling apparatus with surgical stapling assembly.

FIG. 2 illustrates a surgical stapling apparatus with a surgical stapling assembly. The surgical stapling apparatus includes a handle 9, an elongate insertion sleeve 10 extending from the handle and the surgical stapling assembly 4 at the distal end of the handle where the elongate sleeve is slidably disposed over the surgical stapling assembly. The stapling assembly is releasably secured to a distal end of the elongate body of the stapling apparatus. The surgical stapling assembly comprises a driver having a housing 5 and having a proximal and a distal end and at least one staple 6 having a proximal end and a distal end that is loaded within the driver. The elongate sleeve 10 has proximal and distal ends with a plurality of prongs 11 on the distal end of the elongate sleeve. The surgical stapling apparatus also includes an activation button 12 contained within the handle.

The driver may also include a cocking spring-loaded hammer (not shown) to drive a staple through the augmentation sheet and into tendon or bone, fixing the sheet to the tendon or bone. The sleeve may be pressed against the augmentation sheet, and the driver advances forward through the sleeve, and through the augmentation sheet affixing it to the tendon or bone. The tip of the sleeve holds the augmentation sheet stable and prevents it from slipping or tenting. The distal end of the sleeve may have prongs or serrations to help hold the augmentation sheet flat while the driver pushes the staple through the sheet and fixes the sheet to the tendon or bone. The staple is driven into the tendon or bone and the barbs prevent the staple from backing out of the desired position. This ensures that the augmentation sheet and the tendon tissue is firmly held together and ensures that the staple does not shift from the desired position and maintains the staple alignment when in position.

Figure 3A:
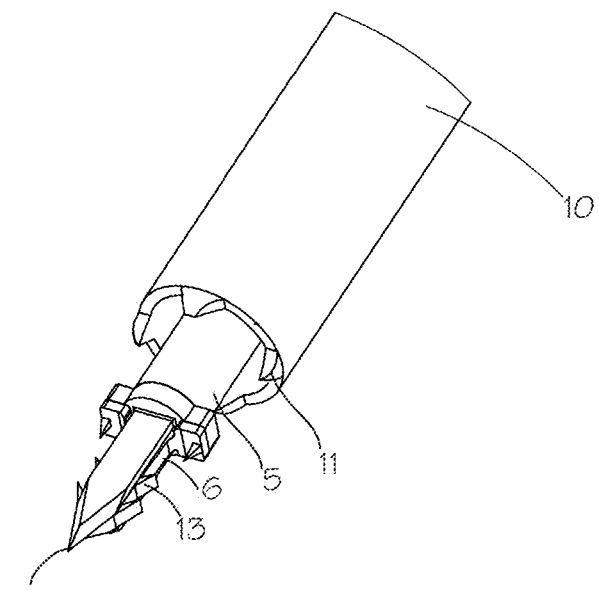
FIGS. 3a and 3b show the driver of the surgical stapling assembly.
Figure 3B:
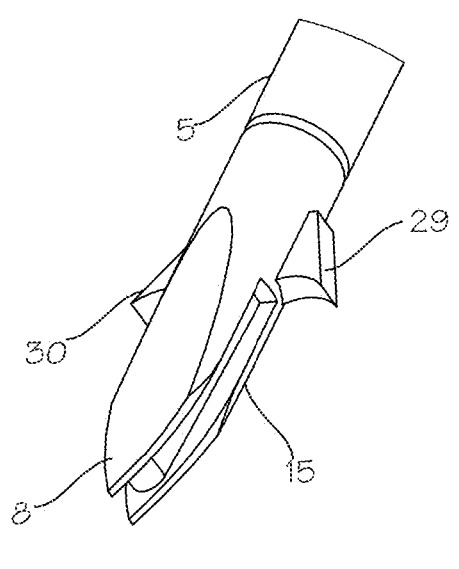

FIGS. 3a and 3b show the driver of the surgical stapling assembly. FIG. 3a illustrates the driver 5 that includes a staple 6 loaded within the driver housing. Barbs 13 contained on the staple protrude from the driver when in the loaded position. This figure illustrates the elongate sleeve 10, that can be slidably disposed over the driver, and staple at the distal end of the surgical stapling assembly. The driver includes a housing that has a distal end that has a piercing tip 8 or trocar point configured to be inserted into a channel of the staple to releasably engage the staple for insertion into a patient. The driver housing distal end also includes the trocar 8 to serve as a guide that can pierce an augmentation sheet. A drive anvil 15 (shown in FIGS. 3b and 6d) also longitudinally extends within the housing. The driver, drive anvil and pointed trocar 8 are coupled to the activation button 12 which is configured to facilitate extension and retraction of the drive anvil and trocar at the distal end of the body. FIG. 3b illustrates a driver distal tip where there is no staple loaded in the driver. Proximal to the drive anvil 15 is a trocar 8 for correct placement of the staple within the body. Proximal to the trocar is the anvil 15 for support of the staple. The piercing trocar also pierces the augmentation patch so that the staple advances through the augmentation patch without tenting. The anvil 15 is a metal plate and extends through the center of the driver 5. The anvil also includes anvil shoulders 29, 30 that protrude from a proximal end of the anvil. When the driver is inserted into the staple central or inner channel, the staple is releasably secured to the driver by friction or alternatively can be secured by a snap detent. The snap detent can hold the staple to the driver in order to be securely advanced through a patient. The detent can include a spring and a detent that interfaces with the spring via a groove or notch that the detent snaps into. The elongate sleeve is advanced forward to cover the sharp tip of the driver during insertion. The sleeve holds the augmentation patch stable while the staple passes through the tissue and press it against the anvil which bends the staple legs to secure the augmentation patch to tissue.

Figure 4:
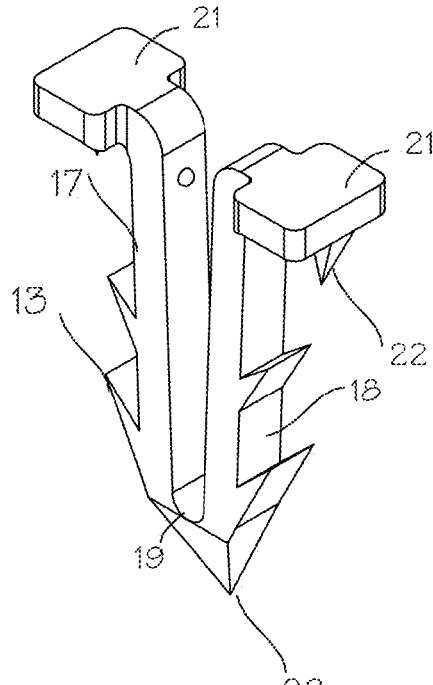
FIG. 4 illustrates a staple for use with the surgical stapling assembly.

FIG. 4 illustrates a staple for use with the surgical stapling assembly. The staple includes a U-shaped inner body having a pair of legs 17, 18 with a bridging portion 19 between the legs. The legs may either be parallel, or alternatively be are at a taper angle to help release the staple from the driver anvil. The bridging portion has an inner and outer surface where the inner surface forms the "U" shape of the staple and the outer portion terminates in a pointed tip 20. The bridging portion is the end of the staple that is loaded onto the driver for insertion into the patient. Opposite the bridging portion, the legs include compression flanges 21 that project from the legs and prongs 22 projecting from the under-side of the compression legs. The outer surfaces of the legs include a plurality of barbs 13 that project from the outer surface of the legs. The inner "U" shaped body portion is open and creates a channel that allows for tissue growth and prevents the staple from backing out of the bone or tendon when in place. The barbs are configured to engage with soft tissue when inserted into a tendon or hard bone. The legs include the compression flanges 21 at the proximal end of the staple for further securing the staple within the tendon or bone. The outer surface of the bridging portion 19 of the staple is pointed 20 and generally sharp to allow ease of insertion through the augmentation sheet and into bone and body tissue, fixing the augmentation sheet to the target tissue. The bridging portion provides stability and resists bending of the staple as it is advanced through the body. In addition, the bridging portion prevents the staple from sinking too deep or causing damage to the body tissue and gives a visual indication of correct placement depth. The staple can also be over molded over the suture. The staple is configured onto to the drive anvil and next to the trocar when loaded on the driver where activation of the anvil and trocar activates firing of the staple into the tendon or bone. Once the augmentation patch is pierced, the driver then drives a staple through the pierced hole of the augmentation patch to drive the staple into the tendon or bone. The trocar is used to cut a hole in the augmentation patch before insertion so that the augmentation patch does not wad up or bunch up when the staple is driven onto the bone or tendon. The elongate insertion sleeve is advanced over the driver and staple and prongs on the distal end of the sleeve to secure the augmentation patch to prevent tenting away of the augmentation patch from the staple as it is pushed or driven through the bone or tendon. The elongate sleeve functions to protect the tip of the driver so that the driver can be pushed through a cannula seal without the sharp end of the driver snagging on the cannula seal. In a first position the retractable sleeve covers the pointed end of the driver and in a second position retracts from the pointed end to drive the staple and augmentation patch to a predetermined position within the tendon tissue. The elongate sleeve may have a radiused tip to ease passage through the cannula. The staple can be made of any biocompatible material including titanium and its alloys, stainless steel, Nitinol or bioabsorbable polymers. The staple can also be made of any absorbable material such as PLG or PLGA, or a non-absorbable polymer such as PEEK.

Figure 5:
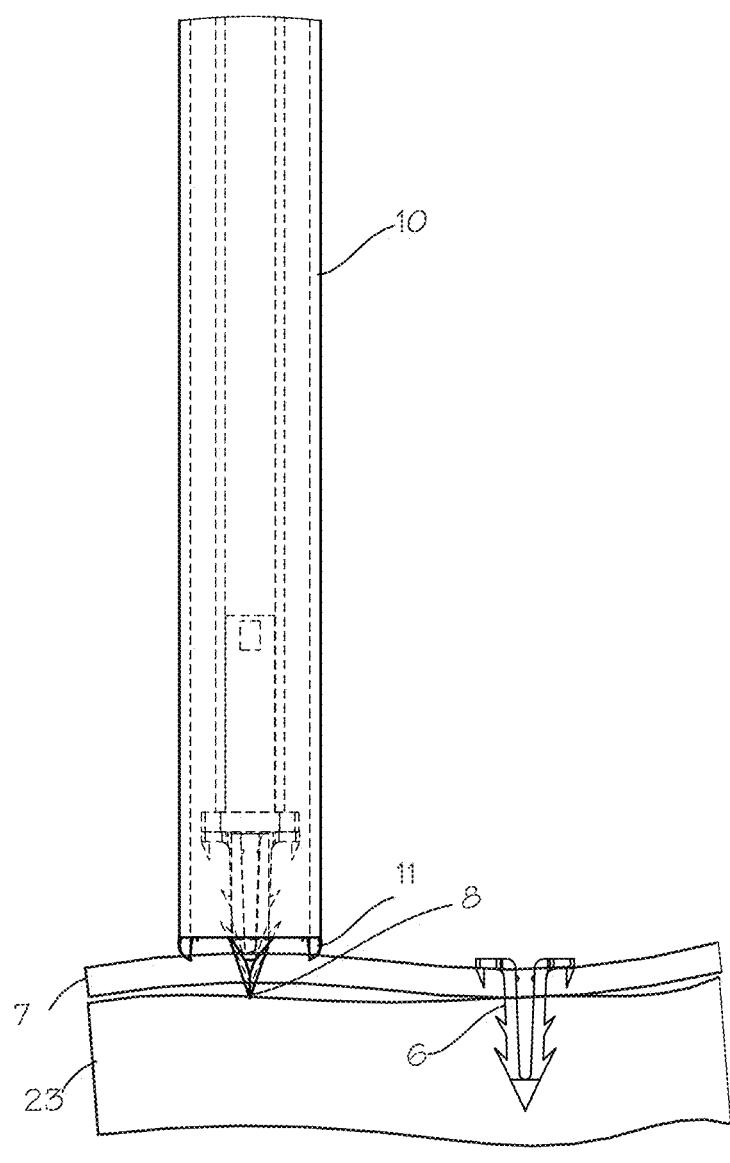
FIG. 5 illustrates a cross sectional view of the driver within the insertion tube piercing an augmentation patch and driving staple into tendon or bone.

FIG. 5 illustrates a cross sectional view of the driver 5 within the elongate insertion sleeve 10 piercing an augmentation patch and driving staple into tendon or bone. This figure illustrates a cross section view of the distal end of the driver as positioned inside the elongate insertion sleeve. This figure illustrates both a staple 6 loaded within the driver housing with the entire assembly. A staple is also illustrated outside of the assembly to show where the staple is positioned relative to the driver. In a loaded position, the staple in inserted on the driver so the inner "U" shaped channel is positioned in the driver distal tip and the outer pointed surface aligns with the driver trocar piercing tip 8. The figure illustrates a staple advanced through a pierced augmentation patch 7 as it is inserted into the tendon or bone 23.

FIG. 6a illustrates the staple 6 when positioned onto the distal end of driver 5 and FIG. 6b is a side view of FIG. 6a. In these views, the staple is loaded onto the driver 5 and the trocar tip 8 is advanced distally of the anvil 15 with the staple compression flanges 21 abutting the anvil. The trocar tip 8 projects distally to the anvil 15 of the driver. The staple 6 is positioned on the distal end of the driver with the staple pointed tip 20 proximal the trocar tip. The anvil is contained centrally within the driver. The staple is advanced onto the distal end of the driver, with the anvil 15 positioned proximal to the driver distal end and behind the staple. The staple is loaded onto the distal end of the driver with the anvil positioned directly behind the staple. The anvil shoulders 29, 30 are laterally spaced relative to the central axis of the driver and define a support surface on either side of the drivers' central axis. Compression flanges 21 of the staple abut against the anvil shoulders of the driver proximal end and barbs 13 project from the outer surface of staple. The pointed trocar 8 extends beyond the staple pointed end 20. In a loaded position, the staple bridging portion engages to the driver where the anvil is contained within the staple inner channel and the staple legs straddle the anvil so that the opposing legs of the staple are positioned around the anvil on the driver. The anvil is centrally positioned and supported by the driver. FIG. 6*c* is a cross sectional view along line A-A of FIG. 6*b*. FIG. 6*c* illustrates the staple loaded onto the anvil of the driver in a loaded position. The drive anvil is positioned within the "U" shaped inner surface of the bridging portion of the staple and the opposing legs of the staple extend from the bridging portion around the drive anvil and are adapted for disposition within the tendon tissue. FIG. 6*d* is a cross sectional view along line B-B of FIG. 6*b*. The cross section illustrates an I-beam drive anvil 15 contained within the housing of the driver 5 that extends longitudinally along the driver housing. The staple is shown relative to the anvil within the driver housing.

Figure 7A:
FIGS. 7a and 7b illustrate alternative staple with an anchor or suture optionally be included in the staple.
Figure 7A:
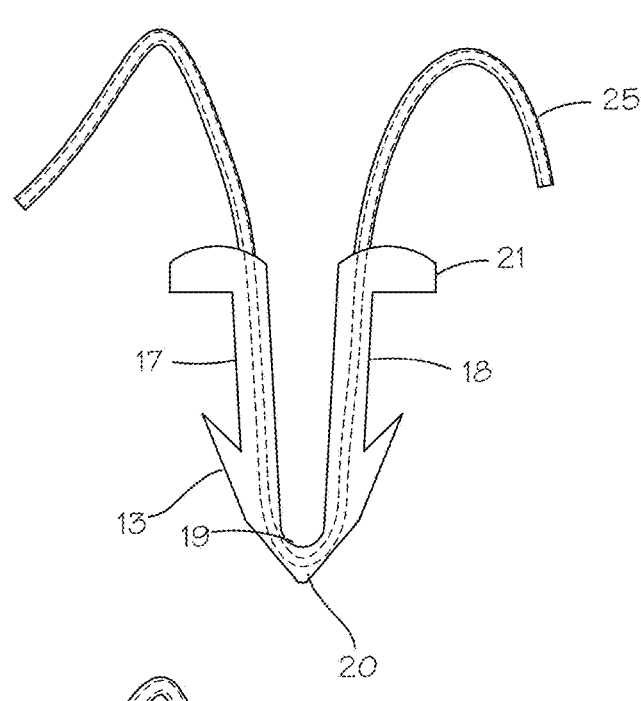
Figure 7B:
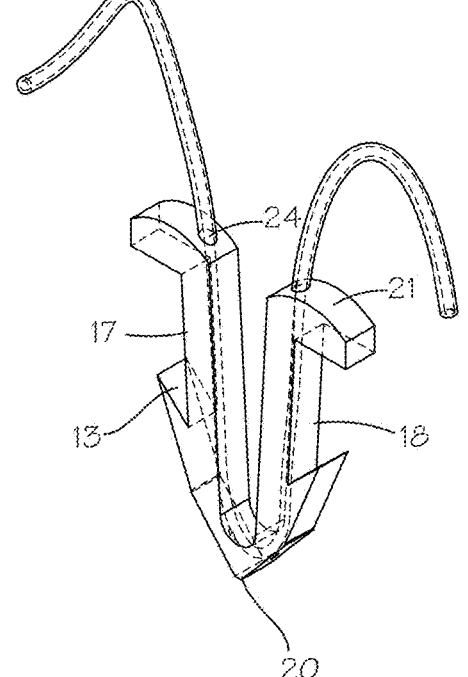

FIGS. 7*a* and 7*b* illustrates alternative staple with an anchor or suture optionally be included in the staple. A channel or eyelet 24 is formed between the extending legs. A suture 25 can be introduced through U-shaped staple via the channel or eyelet formed within the staple frame, through a leg, bridging portion and exiting through the second leg. The staple can include an opening or hole for introduction of the trocar point of the driver.

Figure 8:
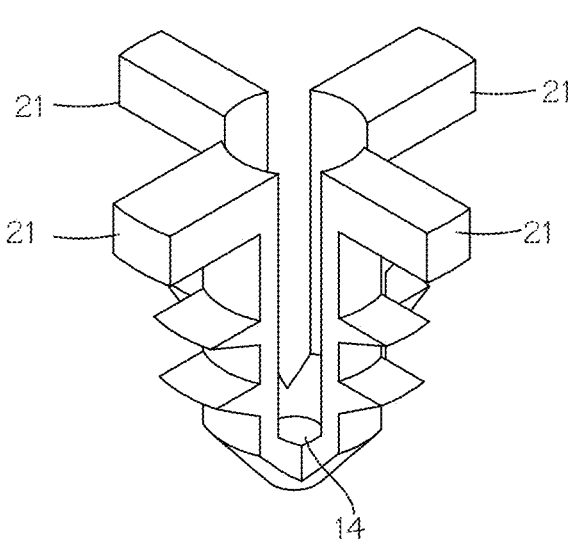
FIG. 8 is a view of an alternative staple configuration where the staple includes a plurality of compression legs.

FIG. 8 a view of an alternative staple configuration where the staple includes a plurality of compression flanges 21. The staple includes a compression table on plurality of opposing legs with barbs projecting from the legs and a hole for a pilot driver hole 14. An inner channel is formed between the plurality of flanges to allow for tissue ingrowth when the staple is in position.

Figure 9:
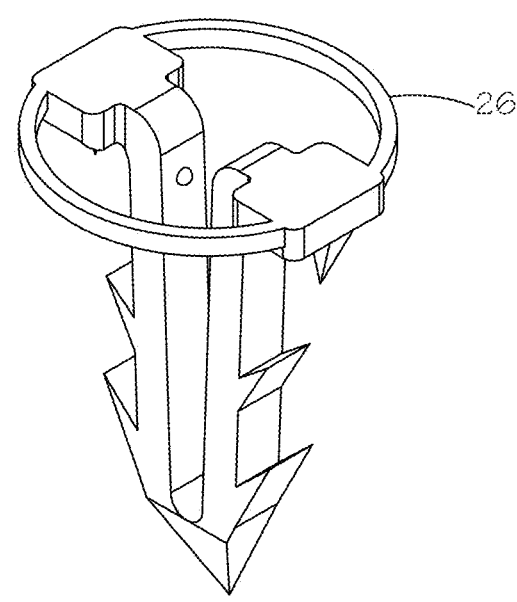
FIG. 9 is a view of another alternative staple configuration that includes an annular hoop or ring connected to the compression flanges and circling the staple.

FIG. 9 is a view of another alternative staple configuration that includes an annular hoop or ring 26 connected to the compression flanges and circling the staple. The ring or hoop provides for additional stiffening and compression area to the staple. The additional hoop provides additional hold down area for the augmentation patch. This generates more side force to push the barbs into the tissue and further prevent back out of the staple and prevent tear through of the augmentation patch.

Figure 10:
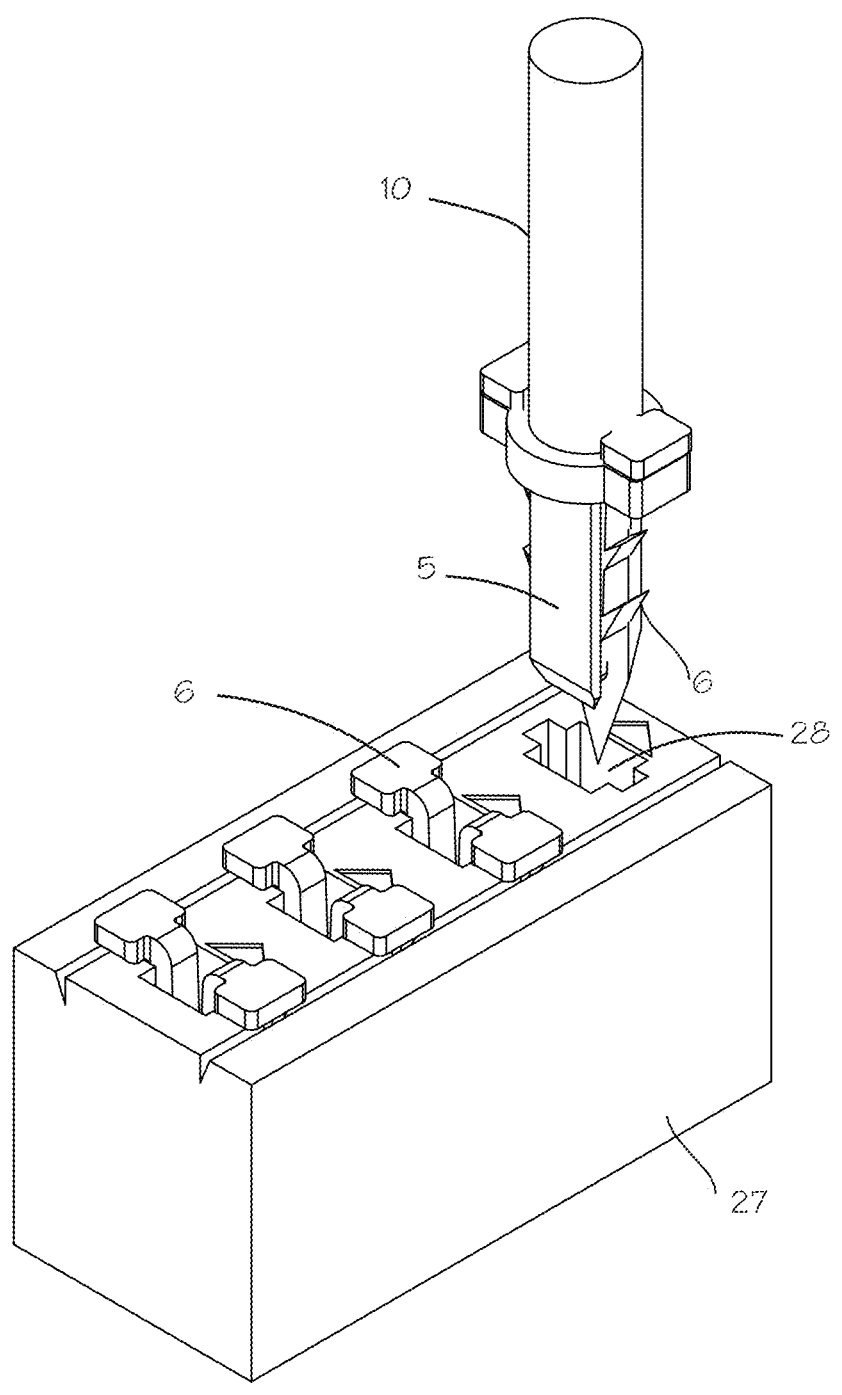
FIG. 10 illustrates a method of staple delivery and placement.

FIG. 10 illustrates a method of staple delivery and placement. In use, a surgical incision is made to create access to target tissue area. A pilot hole is then created in the augmentation sheet, tissue or bone using the pilot hole trocar. The pilot hole is usually smaller than the size of the staple to be inserted and facilitates passage of the staple through the augmentation sheet. Staples are present in a loading cassette holder 27. The driver 5 is inserted into the loading cassette holder to lift a staple 6 from a recess 28 in the holder by the driver. The sleeve is loaded onto the driver anvil and introduced into the surgical workspace. When in the correct position, the sleeve is placed against the augmentation sleeve and the sharp distal tip of the driver pierces the augmentation sleeve and advances the staple. The staple is then pushed or tapped into the tendon or bone with a mallet (not shown) to fix the biological construct into place. The staple cartridge is selected and then loaded into the spring-loaded driver. The driver is then positioned so that the staple aligns with the pilot hole of the driver. The surgeon then activates the driver to fire the staple and drive the anvil and staple into the tissue. The staple is usually pre-formed. Alternatively, when the staple is driven into the tissue or bone, it encounters the anvil, causing it to bend and form the "U" shape at a hinge point, driving it through the augmentation sheet and into the tissue, securely holding the tissue together. Once the staple is fully formed and securely positioned, the driver is removed from the surgical site.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

I claim:

1. A surgical stapling assembly for fixation of an augmentation sheet in tendon tissue repair comprising:
   a driver having an exterior housing, the driver having a proximal end and a distal end, the distal end of the driver includes a trocar piercing tip and a drive anvil longitudinally extending within the housing, wherein the trocar piercing tip extends distally beyond the drive anvil; and
   a staple having a pair of opposing legs with compression flanges projecting from a first end of the staple and a bridging portion between the opposing legs at a second end of the staple, the bridging portion having a "U" shaped inner surface and an outer pointed surface that terminates in a tip, wherein in a loaded configuration, the drive anvil is positioned within the "U" shaped inner surface of the bridging portion of the staple and the opposing legs of the staple extend from the bridging portion around the drive anvil and are adapted for disposition within the tendon tissue;
   wherein the staple further comprises a channel or eyelet between the opposing legs and the channel contains a suture.

2. The surgical stapling assembly of claim 1 wherein the staple is comprised of a material selected from the group of biomaterials consisting of titanium, titanium alloy, stainless steel, nitinol, bioabsorbable polymers and non-absorbable biocompatible polymers.

3. The surgical stapling assembly of claim 1 wherein the drive anvil is an I-beam anvil.

4. The surgical stapling assembly of claim 1 wherein the staple further includes a plurality of barbs projecting from the compression flanges.

* * * * *